US009017982B1

(12) United States Patent
Shah et al.

(10) Patent No.: US 9,017,982 B1
(45) Date of Patent: Apr. 28, 2015

(54) NON-WILD-TYPE ORGANOPHOSPHORUS ACID ANHYDROLASES FOR ENZYMATIC DECONTAMINATION

(71) Applicant: U.S. Army Edgewood Chemical and Biological Command, APG, MD (US)

(72) Inventors: Saumil S. Shah, Columbia, MD (US); Mark A. Guelta, White Marsh, MD (US); Steven P. Harvey, Lutherville, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 0 days.

(21) Appl. No.: 14/109,119

(22) Filed: Dec. 17, 2013

Related U.S. Application Data (60) Provisional application No. 61/787,487, filed on Mar. 15, 2013.

(51) Int. Cl.
*C12N 9/18* (2006.01)
*A61K 38/46* (2006.01)
*C12N 9/16* (2006.01)

(52) U.S. Cl.
CPC ................ *A61K 38/465* (2013.01); *C12N 9/16* (2013.01)

(58) Field of Classification Search
CPC combination set(s) only.
See application file for complete search history.

*Primary Examiner* — Kagnew H Gebreyesus
(74) *Attorney, Agent, or Firm* — Ulysses John Biffoni

(57) ABSTRACT

Provided are non-wild-type organophosphorus acid anhydrolases that are capable of degrading (ethyl {2-[bis(propan-2-yl)amino]ethyl}sulfanyl) (methyl)phosphinate and other V-agents. Particular embodiments include an organophosphorus acid anhydrolase including an amino acid substitution at position 212.

4 Claims, 2 Drawing Sheets

NON-WILD-TYPE ORGANOPHOSPHORUS ACID ANHYDROLASES FOR ENZYMATIC DECONTAMINATION

CROSS-REFERENCE TO RELATED APPLICATIONS

This application claims the benefit of priority from U.S. provisional application Ser. No. 61/787,487 filed on Mar. 15, 2013.

GOVERNMENT INTEREST

The invention described herein may be manufactured, used, and licensed by or for the United States Government.

FIELD OF THE INVENTION

The invention relates to novel enzymes with highly tailored capability to degrade one or more toxins. More specifically, the invention is related to organophosphorus acid anhydrolase mutants capable of degrading (Ethyl {2-[bis(propan-2-yl)amino]ethyl}sulfanyl) (methyl)phosphinate.

BACKGROUND OF THE INVENTION

Enzymes can provide extraordinary protection against toxic compounds. The enzymatic detoxification of malathion is one example. Malathion is a very effective insecticide when used against fruit flies, yet it has very little toxic effect on humans due to its detoxification in the liver by the enzyme carboxylesterase. The species and target selectivity provided by enzymes allows for uses in a variety of complex backgrounds with little to no risk of harm to desirable organisms or components in the background.

VX ((Ethyl {2-[bis(propan-2-yl)amino]ethyl}sulfanyl) (methyl)phosphinate is one of the most toxic compounds known in humans. The median lethal dose ($LD_{50}$) for humans is estimated to be about 10 milligrams when contact is through skin. The estimated $LCt_{50}$ for inhalation is estimated to be 30-50 mg·min/m$^3$. No efficient and easily produced catalyst for VX degradation in the environment or in vivo is known. One enzyme, phosphotriesterase (PTE), also known as organophosphorus hydrolase (OPH), has previously been reported to possess VX activity. However, PTE is not easily produced in bacteria at high concentrations necessitating more complex synthesis procedures and increasing the difficulty of obtaining sufficient, active quantities of the enzyme to be useful in an environmental setting.

As such, new compounds and methods for the specific degradation of VX are needed.

SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

Provided are non-wild type organophosphorus acid anhydrolase proteins that include a non-wild-type amino acid at sequence position 212, optionally at position 212 of SEQ ID NO: 1. A non-wild type organophosphorus acid anhydrolase protein optionally has the sequence of SEQ ID NO: 2, or a catalytically active fragment thereof. The protein is optionally isolated. The wild-type amino acid at position 212 is optionally substituted with a G, F, P, Q, or T. The non-wild type organophosphorus acid anhydrolase protein optionally has increased catalytic activity for the degradation of (ethyl {2-[bis(propan-2-yl)amino]ethyl}sulfanyl) (methyl)phosphinate relative to the wild-type enzyme. The catalytic activity of the non-wild type protein is optionally 2-fold or greater relative to a protein having the wild-type sequence, optionally to a protein having SEQ ID NO: 1 or SEQ ID NO: 2 with Y212F.

Also provided are processes of degrading (ethyl {2-[bis(propan-2-yl)amino]ethyl}sulfanyl) (methyl)phosphinate including contacting (ethyl {2-[bis(propan-2-yl)amino]ethyl}sulfanyl) (methyl)phosphinate with a non-wild-type organophosphorus acid anhydrolase protein having a non-wild-type amino acid at sequence position 212, optionally at position 212 of SEQ ID NO: 1. A non-wild type organophosphorus acid anhydrolase protein optionally has the sequence of SEQ ID NO: 2, or a catalytically active fragment thereof. The protein is optionally isolated. The wild-type amino acid at position 212 is optionally substituted with a G, F, P, Q, or T. The non-wild type organophosphorus acid anhydrolase protein optionally has increased catalytic activity for the degradation of (ethyl {2-[bis(propan-2-yl)amino]ethyl}sulfanyl) (methyl)phosphinate relative to the wild-type enzyme. The catalytic activity of the non-wild type protein is optionally 2-fold or greater relative to a protein having the wild-type sequence, optionally to a protein having SEQ ID NO: 1 or SEQ ID NO: 2 with Y212F. The processes are optionally performed in vivo. Optionally, the (ethyl {2-[bis(propan-2-yl)amino]ethyl}sulfanyl) (methyl)phosphinate is in a subject, optionally a cell, a human or a non-human animal.

Kits are also provided for the degradation of (ethyl {2-[bis(propan-2-yl)amino]ethyl}sulfanyl) (methyl)phosphinate that include a non-wild-type organophosphorus acid anhydrolase protein including a non-wild-type amino acid at sequence position 212 and a pharmaceutically acceptable carrier. The non-wild type protein optionally has a substitution at position 212 of SEQ ID NO: 1. A non-wild type organophosphorus acid anhydrolase protein optionally has the sequence of SEQ ID NO: 2, or a catalytically active fragment thereof. The protein is optionally isolated. The wild-type amino acid at position 212 is optionally substituted with a G, F, P, Q, or T. The non-wild type organophosphorus acid anhydrolase protein optionally has increased catalytic activity for the degradation of (ethyl {2-[bis(propan-2-yl)amino]ethyl}sulfanyl) (methyl)phosphinate relative to the wild-type enzyme. The catalytic activity of the non-wild type protein is optionally 2-fold or greater relative to a protein having the wild-type sequence, optionally to a protein having SEQ ID NO: 1 or SEQ ID NO: 2 with Y212F.

DETAILED DESCRIPTION OF EMBODIMENTS OF THE INVENTION

Figure 1:
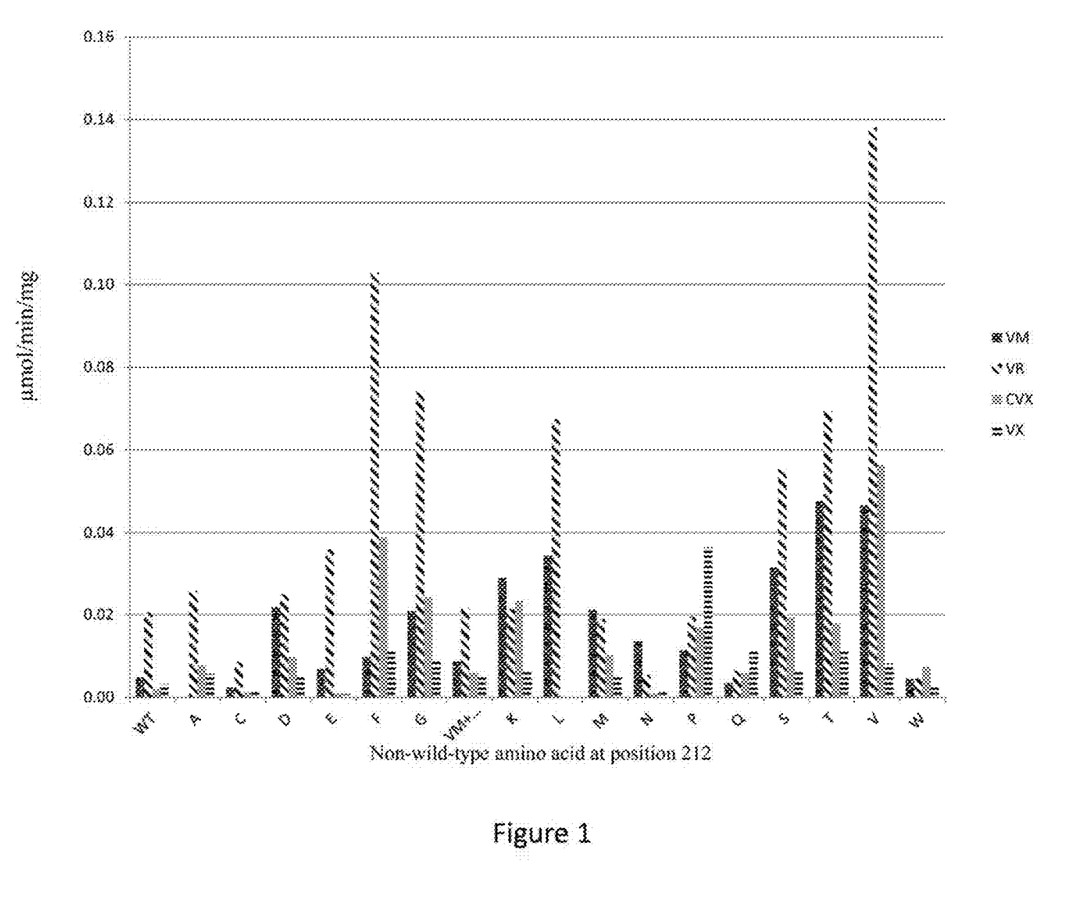
FIG. 1 illustrates the catalytic activity of OPAA mutants with various substitutions at position 212.
Figure 2:
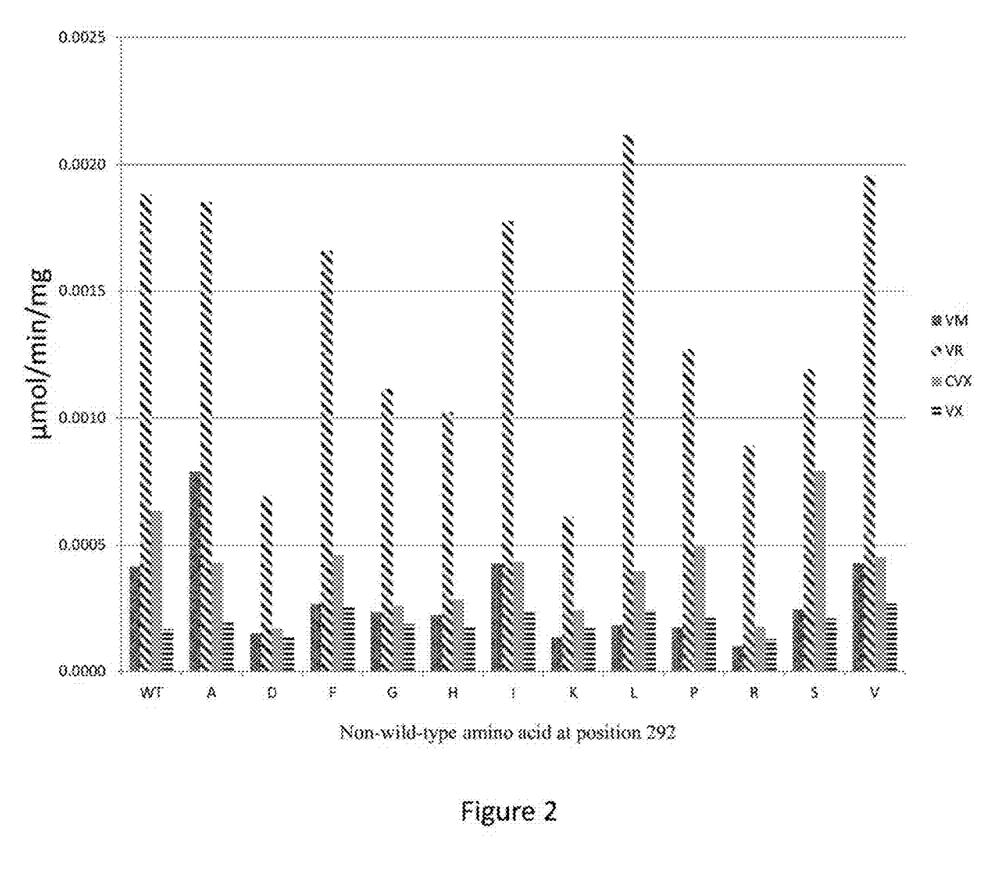
FIG. 2 illustrates the catalytic activity of OPAA mutants with various substitutions at position 292.

The following description of particular embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the compositions are described as using specific materials in a particular order, it is appreciated that the described materials or order may be interchangeable such that the description of the invention includes multiple parts or steps arranged in many ways as is readily appreciated by one of skill in the art.

The invention has utility as a composition for the catalytic degradation of (Ethyl {2-[bis(propan-2-yl)amino]ethyl}sulfanyl) (methyl)phosphinate (VX). The inventors discovered that the enzyme organophosphorus acid anhydrolase (OPAA), which in wild-type form is unable to catalyze the degradation of VX, can be mutated to alter its substrate specificity to act on VX causing its degradation. This invention describes mutant versions of OPAA which are easily produced at very high concentrations in *E. coli*.

Native OPAA was originally derived from the bacterium *Altermonas* sp. JD6.5 and its gene has subsequently been cloned into *E. coli*. The native OPAA enzyme has been described to possess catalytic activity against various chemical nerve agents but no activity against the particularly toxic and persistent agent VX was ever observed. Native OPAA has the amino acid sequence of:

```
                                                         (SEQ ID NO: 1)
  1  MNKLAVLYAE HIATLQKRTR EIIERENLDG VVFHSGQAKR QFLDDMYYPF

51  KVNPQFKAWL PVIDNPHCWI VANGTDKPKL IFYRPVDFWH KVPDEPNEYW

101  ADYFDIELLV KPDQVEKLLP YDKARFAYIG EYLEVAQALG FELMNPEPVM

151  NFYHYHRAYK TQYELACMRE ANKIAVQGHK AARDAFFQGK SEFEIQQAYL

201  LATQHSENDN AYGNIVALNE NCAILHYTHF DRVAPATHRS FLIDAGANFN

251  GYAADITRTY DFTGEGEFAE LVATMKQHQI ALCNQLAPGK LYGELHLDCH

301  QRVAQTLSDF NIVDLSADEI VAKGITSTFF PHGLGHHIGL QVHDVGGFMA

351  DEQGAHQEPP EGHPFLRCTR KIEANQVFTI EPGLYFIDSL LGDLAATDNN

401  QHINWDKVAE LKPFGGIRIE DNIIVHEDSL ENMTRELRAR LTTHSLRGLS

451  APQFSINDPA VMSEYSYPSE PLSYEEEIKK STFIVHVRTR RILVRRRTLS

501  PILIAVTPMP AITAGLM
```

The inventors discovered that OPAA having a mutation at amino acid 212 will convert this enzyme into a VX catalyzing compound. One particular mutation, Y212F, whereby a tyrosine is replaced by a phenylalanine at position 212, catalyzes the degradation of VX with excellent specific activity. This will allow mutant OPAA enzymes to be used for in vivo treatment of VX poisoning or for the catalytic decontamination of VX from surfaces or in the environment.

A mutant OPAA is provided. A mutant OPAA having catalytic activity against VX includes one or more mutations in the active site that include a mutation at Y212. In some embodiments, an OPAA includes the mutation at Y212 where the Y is substituted with a G, F, P, Q or T. In some embodiments, a mutant OPAA has the sequence of:

Optionally, a non-wild-type OPAA includes one or more mutations, optionally with 2, 3, 4, 5, 6, 7, 8 or more non-wild-type amino acid residues with the proviso that at least one of the non-wild-type amino acid residues is present at position 212. Optionally, a non-wild-type OPAA has a wild-type amino acid at position 292.

A non-wild-type OPAA has a non-wild-type amino acid at residue 212 where the non-wild-type amino acid is G, F, P, Q or T. A non-wild-type OPAA optionally has additional non-wild-type amino acid substitutions, includes a deletion, or an additional amino acid sequence contained within the non-wild-type OPAA sequence.

In some embodiments, a non-wild-type OPAA is a fragment of wild-type OPAA where the fragment includes sufficient residues of OPAA to include the active site.

Amino acids present in a non-wild-type OPAA optionally include the common amino acids alanine, cysteine, aspartic acid, glutamic acid, phenylalanine, glycine, histidine, isoleucine, lysine, leucine, methionine, asparagine, proline, glutamine, arginine, serine, threonine, valine, tryptophan, and tyrosine as well as less common naturally occurring amino acids, modified amino acids or synthetic compounds, such as alpha-asparagine, 2-aminobutanoic acid or 2-aminobutyric acid, 4-aminobutyric acid, 2-aminocapric acid (2-aminodecanoic acid), 6-aminocaproic acid, alpha-glutamine, 2-aminoheptanoic acid, 6-aminohexanoic acid, alpha-aminoisobutyric acid (2-aminoalanine), 3-aminoisobutyric acid, beta-alanine, allo-hydroxylysine, allo-sioleucine, 4-amino-7-methylheptanoic acid, 4-amino-5-phe-

```
                                                         (SEQ ID NO: 2)
  1  MNKLAVLYAE HIATLQKRTR EIIERENLDG VVFHSGQAKR QFLDDMYYPF

51  KVNPQFKAWL PVIDNPHCWI VANGTDKPKL IFYRPVDFWH KVPDEPNEYW

101  ADYFDIELLV KPDQVEKLLP YDKARFAYIG EYLEVAQALG FELMNPEPVM

151  NFYHYHRAYK TQYELACMRE ANKIAVQGHK AARDAFFQGK SEFEIQQAYL

201  LATQHSENDT PFGNIVALNE NCAILHYTHF DRVAPATHRS FLIDAGANFN

251  GYAADITRTY DFTGEGEFAE LVATMKQHQI ALCNQLAPGK LYGELHLDCH

301  QRVAQTLSDF NIVNLSADEI VAKGITSTFF PHGLGHHIGL QVHDVGGFMA

351  DEQGAHQEPP EGHPFLRCTR KIEANQVFTI EPGLYFIDSL LGDLAATDNN

401  QHINWDKVAE LKPFGGIRIE DNIIVHEDSL ENMTRELELD
``` nylpentanoic acid, 2-aminopimelic acid, gamma-amino-beta-hydroxybenzenepentanoic acid, 2-aminosuberic acid, 2-carboxyazetidine, beta-alanine, beta-aspartic acid, biphenylalanine, 3,6-diaminohexanoic acid, butanoic acid, cyclobutyl alanine, cyclohexylalanine, cyclohexylglycine, N5-aminocarbonylornithine, cyclopentyl alanine, cyclopropyl alanine, 3-sulfoalanine, 2,4-diaminobutanoic acid, diaminopropionic acid, 2,4-diaminobutyric acid, diphenyl alanine, NN-dimethylglycine, diaminopimelic acid, 2,3-diaminopropanoic acid, S-ethylthiocysteine, N-ethylasparagine, N-ethylglycine, 4-aza-phenylalanine, 4-fluoro-phenylalanine, gamma-glutamic acid, gamma-carboxyglutamic acid, hydroxyacetic acid, pyroglutamic acid, homoarginine, homocysteic acid, homocysteine, homohistidine, 2-hydroxyisovaleric acid, homophenylalanine, homoleucine, homoproline, homoserine, homoserine, 2-hydroxypentanoic acid, 5-hydroxylysine, 4-hydroxyproline, 2-carboxyoctahydroindole, 3-carboxyisoquinoline, isovaline, 2-hydroxypropanoic acid (lactic acid), mercaptoacetic acid, mercaptobutanoic acid, sarcosine, 4-methyl-3-hydroxyproline, mercaptopropanoic acid, norleucine, nipecotic acid, nortyrosine, norvaline, omega-amino acid, ornithine, penicillamine (3-mercaptovaline), 2-phenylglycine, 2-carboxypiperidine, sarcosine (N-methylglycine), 2-amino-3-(4-sulfophenyl)propionic acid, 1-amino-1-carboxycyclopentane, 3-thienylalanine, epsilon-N-trimethyllysine, 3-thiazolylalanine, thiazolidine 4-carboxylic acid, alpha-amino-2,4-dioxopyrimidinepropanoic acid, and 2-naphthylalanine.

Modifications and changes can be made in the structure of the inventive non-wild-type OPAA that are the subject of the application and still obtain a molecule having similar or improved characteristics as the Y212 mutated sequence (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like or improved properties. Optionally, a polypeptide is used that has less or more activity compared to the Y212 mutant sequence.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In making such changes, the substitution of amino acids whose hydropathic indices are within ±2 is optional, those within ±1 are optional, and those within ±0.5 are similarly optional.

Substitution of like amino acids can also be made on the basis of hydrophilicity, particularly where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is optional, those within ±1 are optional, and those within ±0.5 are optional.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of polypeptides can include variants having about 50%, 69%, 70%, 80%, 90%, and 95% sequence identity to the protein of SEQ ID NO: 1, or other Y212 mutants where Y is substituted by G, F, P, Q or T.

It is appreciated that amino acids are optionally L- or D-isomers. An inventive non-wild-type OPAA optionally includes mixtures of L- and D-isomers.

A non-wild-type OPAA is obtained by any of various methods known in the art illustratively including isolation from a cell or organism, chemical synthesis, expression of a nucleic acid sequence, and partial hydrolysis of larger OPAA sequences. Chemical methods of peptide synthesis are known in the art and include solid phase peptide synthesis and solution phase peptide synthesis or by the method of Hackeng, T M, et al., *Proc Natl Acad Sci U S A*, 1997; 94(15):7845-50 or those reviewed by Miranda, L P, *Peptide Science*, 2000, 55:217-26 and Kochendoerfer G G, *Curr Opin Drug Discov Devel*. 2001; 4(2):205-14. In some embodiments, the polypeptide sequences are chemically synthesized by Fmoc synthesis.

Alternatively, synthesis and expression of non-wild-type OPAA is illustratively accomplished from transcription of a nucleic acid sequence encoding a peptide of the invention, and translation of RNA transcribed from nucleic acid sequence, modifications thereof, or fragments thereof. Protein expression is optionally performed in a cell based system such as in *E. coli*, Hela cells, or Chinese hamster ovary cells. It is appreciated that cell-free expression systems are similarly operable.

Further aspects of the present disclosure concern the purification, and in particular embodiments, the substantial purification, of a non-wild-type OPAA protein. The term "purified" or "isolated" as used herein, is intended to refer to a composition, isolatable from other components, wherein the non-wild-type OPAA is purified to any degree relative to its naturally-obtainable state. A purified non-wild-type OPAA, therefore, also refers to a non-wild-type OPAA free from the environment in which it may naturally occur.

Generally, "purified" or "isolated" will refer to a non-wild-type OPAA composition that has been subjected to fractionation to remove various other components, and which composition substantially retains its expressed biological activity. Where the term "substantially" purified is used, this designation will refer to a composition in which the protein or peptide forms the major component of the composition, such as constituting about 50% or more of the proteins in the composition.

Various methods for quantifying the degree of purification of a protein are known to those of skill in the art in light of the present disclosure as based on knowledge in the art. These include, for example, determining the specific activity of an active fraction, or assessing the number of peptides within a fraction by SDS/PAGE analysis. An illustrative method for assessing the purity of a fraction is to calculate the specific activity of the fraction, to compare it to the specific activity of the initial extract, and to thus calculate the degree of purity, herein assessed by a "-fold purification number". The actual units used to represent the amount of activity will, of course, be dependent upon the particular assay technique chosen to follow the purification and whether or not the expressed protein or peptide exhibits a detectable activity.

Various techniques suitable for use in peptide purification will be well known to those of skill in the art. These include, for example, precipitation with ammonium sulphate, polyethylene glycol, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein.

Additional methods of protein isolation illustratively include column chromatography, affinity chromatography, gel electrophoresis, filtration, or other methods known in the art. In some embodiments, a non-wild-type OPAA is expressed with a tag operable for affinity purification. An illustrative tag is a 6× His tag. A 6× His tagged inventive protein is illustratively purified by Ni-NTA column chromatography or using an anti-6× His tag antibody fused to a solid support. (Geneway Biotech, San Diego, Calif.) Other tags and purification systems are similarly operable.

It is appreciated that an inventive protein is optionally not tagged. In this embodiment and other embodiments purification is optionally achieved by methods known in the art illustratively including ion-exchange chromatography, affinity chromatography using antibodies directed to the peptide sequence of interest, precipitation with salt such as ammonium sulfate, streptomycin sulfate, or protamine sulfate, reverse chromatography, size exclusion chromatography such as gel exclusion chromatography, HPLC, immobilized metal chelate chromatography, or other methods known in the art. One of skill in the art may select the most appropriate isolation and purification techniques without departing from the scope of this invention.

There is no general requirement that the non-wild-type OPAA always be provided in its most purified state. It is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater-fold purification than the same technique utilizing a low pressure chromatography system. Methods exhibiting a lower degree of relative purification may have advantages in total recovery of protein product, or in maintaining the activity of an expressed protein.

It is known that the migration of a protein can vary, sometimes significantly, with different conditions of SDS/PAGE (Capaldi et al., *Biochem. Biophys. Res. Comm.,* 76:425, 1977). It will, therefore, be appreciated that under differing electrophoresis conditions, the apparent molecular weights of purified or partially purified expression products may vary.

Non-wild-type OPAA proteins or peptides of this invention may optionally be characterized by measurements including, without limitation, western blot, marcomolecular mass determinations by biophysical determinations, SDS-PAGE/staining, HPLC and the like, antibody recognition assays, activity assays against various possible substrates illustratively including but not limited to VX, VR (N,N-diethyl-2-(methyl-(2-methylpropoxy)phosphoryl)sulfanylethanamine), or VM N,N-diethyl-2-(methyl-(2-methylpropoxy)phosphoryl)sulfanylethanamine).

Also provided are isolated nucleic acids encoding the desired protein sequence analogues thereof, or fragments thereof. These nucleic acids can be used to produce the non-wild-type OPAAs of this invention. It is appreciated that as the nucleic acid code is well known, that one of ordinary skill in the art readily and immediately understands the nucleic acid sequence encoding a desired protein sequence. Thus, a description of a protein sequence is equally a description of an underlying nucleic acid sequence encoding the protein sequence.

The term "nucleotide" is intended to mean a base-sugar-phosphate combination either natural or synthetic, linear, circular and sequential arrays of nucleotides and nucleosides, e.g. cDNA, genomic DNA, mRNA, and RNA, oligonucleotides, oligonucleosides, and derivatives thereof. Included in this definition are modified nucleotides which include additions to the sugar-phosphate groups as well as to the bases.

The term "nucleic acid" or "polynucleotide" refers to multiple nucleotides attached in the form of a single or double stranded polynucleotide that can be natural, or derived synthetically, enzymatically, and by cloning methods. The term "oligonucleotide" refers to a polynucleotide of less than 200 nucleotides. The terms "nucleic acid" and "oligonucleotide" may be used interchangeably in this application.

A nucleic acid as used herein refers to single- or double-stranded molecules that may be DNA, including of the nucleotide bases A, T, C and G, or RNA, comprised of the bases A, U (substitutes for T), C, and G. The nucleic acid may represent a coding strand or its complement. Nucleic acids may be identical in sequence to the sequence naturally occurring, illustratively a sequence encoding SEQ ID NO: 1, or may include alternative codons that encode the same amino acid as that found in the naturally occurring sequence. Furthermore, nucleic acids may include codons that represent conservative substitutions of amino acids as are well known in the art.

One exemplary nucleic sequence encoding a Y212F mutant OPAA is:

(SEQ ID NO: 3)

```
atgaacaaactggcggtgctgtatgcggaacatattgcgaccctgcagaaacgcacccgc gaaattattgaacgcgaaaacctggatggcgtggtgtttcatagcggccaggcgaaacgc cagtttctggatgatatgtattatccgtttaaagtgaacccgcagtttaaagcgtggctg ccggtgattgataaccogcattgctggattgtggcgaacggcaccgataaaccgaaactg atttttatcgcccggtggattttggcataaagtgccggatgaaccgaacgaatattgg gcggattattttgatattgaactgctggtgaaaccggatcaggtggaaaaactgctgccg tatgataaagcgcgctttgcgtatattggcgaatatctggaagtggcgcaggcgctgggc tttgaactgatgaacccggaaccggtgatgaactttatcattatcatcgcgcgtataaa acccagtatgaactggcgtgcatgcgcgaagcgaacaaaattgcggtgcagggccataaa gcggcgcgcgatgcgtttttttcagggcaaaagcgaatttgaaattcagcaggcgtatctg ctggcgacccagcatagcgaaaacgatacccogtttggcaacattgtggcgctgaacgaa aactgcgcgattctgcattatcccattttgatcgcgtggcgccggcgacccatcgcagc tttctgattgatgcgggcgcgaactttaacggctatgcggcggatattacccgcacctat gattttaccggcgaaggcgaatttgcggaactggtggcgaccatgaaacagcatcagatt gcgctgtgcaaccagctggcgccgggcaaactgtatggcgaactgcatctggattgccat cagcgcgtggcgcagaccctgagcgattttaacattgtgaacctgagcgcggatgaaatt gtggcgaaaggcattaccagcacctttttttccgcatggcctgggccatcatattggcctg caggtgcatgatgtgggcggctttatggcggatgaacagggcgcgcatcaggaaccgccg gaaggccatccgtttctgcgctgcacccgcaaaattgaagcgaaccaggtgtttaccatt gaaccgggcctgtatttattgatagcctgctgggcgatctggcggcgaccgataacaac cagcatattaactgggataaagtggcggaactgaaaccgtttggcggcattcgcattgaa gataacattattgtgcatgaagatagcctggaaaacatgacccgcgaactggaactggat.
```

The nucleic acid encoding the non-wild-type OPAA of this invention can be part of a recombinant nucleic acid construct comprising any combination of restriction sites and/or functional elements as are well known in the art that facilitate molecular cloning and other recombinant DNA manipulations. Thus, the present invention further provides a recombinant nucleic acid construct comprising a nucleic acid encoding a non-wild-type OPAA protein or peptide of this invention.

The present invention also provides a vector with a nucleic acid sequence encoding an inventive non-wild-type OPAA. Illustrative vectors include a plasmid, cosmid, cationic lipids, non-liposomal cationic vectors, cationic cyclodextrin, viruses with RNA or DNA genetic material, polyethylenimines, histidylated polylysine, or other vector system known in the art. A vector is optionally a plasmid. A suitable vector optionally possesses cell type specific expression or other regulatory sequences or sequences operable to stimulate or inhibit gene or protein expression. A vector illustratively contains a selection marker such as an antibiotic resistance gene.

The inventive nucleic acid sequence is optionally isolated from the cellular materials with which it is naturally associated. As used herein, the term "isolated nucleic acid" means a nucleic acid separated or substantially free from at least some of the other components of the naturally occurring organism, for example, the cell structural components commonly found associated with nucleic acids in a cellular environment and/or other nucleic acids. The isolation of nucleic acids is optionally accomplished by techniques such as cell lysis followed by phenol plus chloroform extraction, followed by ethanol precipitation of the nucleic acids. The nucleic acids of this invention can be isolated from cells according to methods well known in the art for isolating nucleic acids. Alternatively, the nucleic acids of the present invention can be synthesized according to standard protocols well described in the literature for synthesizing nucleic acids. Modifications to the nucleic acids of the invention are also contemplated, provided that the essential structure and function of the peptide encoded by the nucleic acid are maintained.

Numerous methods are known in the art for the synthesis and production of nucleic acid sequences illustratively including cloning and expression in cells such as *E. coli*, insect cells such as Sf9 cells, yeast, and mammalian cell types such as Hela cells, Chinese hamster ovary cells, or other cells systems known in the art as amendable to transfection and nucleic acid and/or protein expression. Methods of nucleic acid isolation are similarly recognized in the art. Illustratively, plasmid DNA amplified in *E. coli* is cleaved by suitable restriction enzymes such as NdeI and XhoI to linearize PA DNA. The PA DNA is subsequently isolated following gel electrophoresis using a S.N.A.P.™ UV-Free Gel Purification Kit (Invitrogen, Carlsbad, Calif.) as per the manufacturer's instructions.

Numerous agents are amenable to facilitate cell transfection illustratively including synthetic or natural transfection agents such as LIPOFECTIN, baculovirus, naked plasmid or other DNA, or other systems known in the art.

The nucleic acid sequences of the invention may be isolated or amplified by conventional uses of polymerase chain reaction or cloning techniques such as those described in conventional texts. For example, the nucleic acid sequences of this invention may be prepared or isolated from DNA using DNA primers and PCR techniques. Alternatively, the inventive nucleic acid sequence may be obtained from gene banks derived from whole genomic DNA. These sequences, fragments thereof, modifications thereto and the full-length sequences may be constructed recombinantly using conventional genetic engineering or chemical synthesis techniques or PCR, and the like.

Recombinant or non-recombinant proteinase peptides or recombinant or non-recombinant proteinase inhibitor peptides or other non-peptide proteinase inhibitors can also be used in the present invention. Proteinase inhibitors are optionally modified to resist degradation, for example degradation by digestive enzymes and conditions. Techniques for the expression and purification of recombinant proteins are known in the art (see Sambrook Eds., Molecular Cloning: A Laboratory Manual $3^{rd}$ ed. (Cold Spring Harbor, N.Y. 2001).

Some embodiments of the present invention are compositions containing a nucleic acid sequence that can be expressed as a peptide according to the invention. The engineering of DNA segment(s) for expression in a prokaryotic or eukaryotic system may be performed by techniques generally known to those of skill in recombinant expression. It is believed that virtually any expression system may be employed in the expression of the claimed nucleic acid and amino acid sequences.

As used herein, the terms "engineered" and "recombinant" cells are synonymous with "host" cells and are intended to refer to a cell into which an exogenous DNA segment or gene, such as a cDNA or gene encoding as non-wild-type OPAA has been introduced. Therefore, engineered cells are distinguishable from naturally occurring cells which do not contain a recombinantly introduced exogenous DNA segment or gene. A host cell is optionally a naturally occurring cell that is transformed with an exogenous DNA segment or gene or a cell that is not modified. Engineered cells are cells having a gene or genes introduced through the hand of man. Recombinant cells include those having an introduced cDNA or genomic DNA, and also include genes positioned adjacent to a promoter not naturally associated with the particular introduced gene.

To express a recombinant non-wild-type OPAA in accordance with the present invention one optionally prepares an expression vector that comprises a nucleic acid under the control of one or more promoters. To bring a coding sequence "under the control of" a promoter, one positions the 5' end of the translational initiation site of the reading frame generally between about 1 and 50 nucleotides "downstream" of (i.e., 3' of) the chosen promoter. The "upstream" promoter stimulates transcription of the inserted DNA and promotes expression of the encoded recombinant protein. This is the meaning of "recombinant expression" in the context used here.

Many standard techniques are available to construct expression vectors containing the appropriate nucleic acids and transcriptional/translational control sequences in order to achieve peptide expression in a variety of host-expression systems. Cell types available for expression include, but are not limited to, bacteria, such as E. coil and B. subtilis transformed with recombinant phage DNA, plasmid DNA or cosmid DNA expression vectors.

Certain examples of prokaryotic hosts are E. coil strain RR1, E. coli LE392, E. coli B. E. coli .chi. 1776 (ATCC No. 31537) as well as E. coil W3110 (F-, lambda-, prototrophic, ATCC No. 273325); bacilli such as B. subtilis; and other enterobacteriaceae such as Salmonella typhimurium, Serratia marcescens, and various Pseudomonas species.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, E. coli is often transformed using pBR322, a plasmid derived from an E. coli species. Plasmid pBR322 contains genes for ampicillin and tetracycline resistance and thus provides easy means for identifying transformed cells. The pBR322 plasmid, or other microbial plasmid or phage must also contain, or be modified to contain, promoters that can be used by the microbial organism for expression of its own proteins. Another exemplary plasmid vector is the pSE420 vector that includes translation initiation sequences for optimal expression of mammalian genes in E. coli, and an ampicillin resistance gene for selection. The pSE420 vector also includes a lacO operator and lacI repressor for transcriptional regulation.

In addition, phage vectors containing replicon and control sequences that are compatible with the host microorganism can be used as transforming vectors in connection with these hosts. For example, the phage lambda may be utilized in making a recombinant phage vector that can be used to transform host cells, such as E. coil LE392.

Further useful vectors include pIN vectors and pGEX vectors, for use in generating glutathione S-transferase (GST) soluble fusion proteins for later purification and separation or cleavage. Other suitable fusion proteins are those with β-galactosidase, ubiquitin, or the like.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

It is contemplated that the nucleic acids of the disclosure may be "overexpressed", i.e., expressed in increased levels relative to its natural expression in cells of its indigenous organism, or even relative to the expression of other proteins in the recombinant host cell. Such overexpression may be assessed by a variety of methods, including radio-labeling and/or protein purification. However, simple and direct methods are preferred, for example, those involving SDS/PAGE and protein staining or immunoblotting, followed by quantitative analyses, such as densitometric scanning of the resultant gel or blot. A specific increase in the level of the recombinant protein or peptide in comparison to the level in natural human cells is indicative of overexpression, as is a relative abundance of the specific protein in relation to the other proteins produced by the host cell and, e.g., visible on a gel.

A nucleic acid of this invention can be in a cell, which can be a cell expressing the nucleic acid whereby a peptide of this invention is produced in the cell. In addition, the vector of this invention can be in a cell, which can be a cell expressing the nucleic acid of the vector whereby a peptide of this invention is produced in the cell. It is also contemplated that the nucleic acids and/or vectors of this invention can be present in a host animal (e.g., a transgenic animal) which expresses the nucleic acids of this invention and produces the peptides of this invention.

The nucleic acid encoding the non-wild-type OPAA of this invention can be any nucleic acid that functionally encodes the non-wild-type OPAA. To functionally encode the peptides (i.e., allow the nucleic acids to be expressed), the nucleic acid of this invention can include, for example, expression control sequences, such as an origin of replication, a promoter, an enhancer and necessary information processing sites, such as ribosome binding sites, RNA splice sites, polyadenylation sites and transcriptional terminator sequences.

It is further contemplated that a non-wild-type OPAA may be provided for pharmaceutical use. Pharmaceutical compositions optionally include effective amounts of non-wild-type OPAA, or derivative products, together with pharmaceutically acceptable diluents, preservatives, solubilizers, emulsifiers, adjuvants and/or carriers needed for administration. (See PCT 97/01331 for an exemplary listing) The optimal pharmaceutical formulation for a desired biologically active agent will be determined by one skilled in the art depending upon the route of administration and desired dosage. Exemplary pharmaceutical compositions are disclosed in Remington's Pharmaceutical Sciences (Mack Publishing Co., 18th Ed., Easton, Pa., pgs. 1435-1712 (1990)). The pharmaceutical compositions of the present invention may be administered by oral and non-oral preparations (e.g., intramuscular, subcutaneous, transdermal, visceral, IV (intravenous), IP (intraperitoneal), intraarticular, placement in the ear, ICV (intracerebralventricular), IP (intraperitoneal), intraarterial, intrathecal, intracapsular, intraorbital, injectable, pulmonary, nasal, rectal, and uterine-transmucosal preparations).

The non-wild-type OPAA is optionally delivered as naked polypeptide, in aqueous solution, in an emulsion, or in other suitable delivery composition. In some embodiments, the invention is delivered as a component of a pharmaceutical package. Optionally, a protein (or multiple proteins) is present in an emulsion including one or more emulsification agents. In some embodiments, a non-wild-type OPAA is emulsified. Suitable emulsification agents illustratively include supramolecular biovectors (SMBV), nanoparticles such as described by Major, M. et al, *Biochim. Biophys. Acta,* 1997; 1327:32-40, De Migel, I, et al, *Pharm. Res.,* 2000; 17:817-824, U.S. Pat. Nos. 6,017,513, 7,097,849, 7,041,705, 6,979,456, 6,846,917, 6,663,861, 6,544,646, 6,541,030, 6,368,602, Castignolles, N., et el, *Vaccine,* 1996; 14:1353-1360, Prieur, E., et al, *Vaccine,* 1996; 14:511-520, Baudner B, et al, *Infect Immun,* 2002; 70:4785-4790; Liposomes such as described by El Guink et al., *Vaccine,* 1989; 7:147-151, and in U.S. Pat. No. 4,196,191; or other agents known in the art. Agents suitable for use are generally available from Sigma-Aldrich, St. Louis, Mo. The emulsification agent is optionally a dimethyl dioctadecyl-ammonium bromide. Optionally the adjuvant is monophosphoryl lipid A.

Suitable pharmaceutically acceptable carriers facilitate administration of the non-wild-type OPAA are physiologically inert and/or nonharmful. Carriers may be selected by one of skill in the art. Exemplary carriers include sterile water or saline, lactose, sucrose, calcium phosphate, gelatin, dextran, agar, pectin, peanut oil, olive oil, sesame oil, and water. Additionally, the carrier or diluent may include a time delay material, such as glycerol monostearate or glycerol distearate alone or with a wax. In addition, slow release polymer formulations can be used.

Optionally, the inventive composition may also contain conventional pharmaceutical ingredients, such as preservatives, or chemical stabilizers. Suitable ingredients operable herein include, for example, casamino acids, sucrose, gelatin, phenol red, N-Z amine, monopotassium diphosphate, lactose, lactalbumin hydrolysate, and dried milk.

Suitable methods of administration of a non-wild-type OPAA include, but are not limited to intramuscular, intravenous, intranasal, mucosal, oral, parenteral, intravaginal, transdermal, via aerosol delivery or by any route that produces the desired biological effect.

A non-wild-type OPAA protein of the invention is optionally packaged in a single dosage for administration by parenteral (i.e., intramuscular, intradermal or subcutaneous) or nasopharyngeal (i.e., intranasal) administration. The non-wild-type OPAA is optionally delivered by inhalation. The non-wild-type OPAA is optionally combined with a pharmaceutically acceptable carrier to facilitate administration. The carrier is usually water or a buffered saline, with or without a preservative. The non-wild-type OPAA may be lyophilized for resuspension at the time of administration or in solution.

Optional microencapsulation of the inventive non-wild-type OPAA will also provide a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the antigens are all factors that may be considered. Examples of useful polymers illustratively include polycarbonates, polyesters, polyurethanes, polyorthoesters polyamides, poly (d,l-lactide-co-glycolide) (PLGA) and other biodegradable polymers.

The inventive non-wild-type OPAA may additionally contain stabilizers such as thimerosal (ethyl(2-mercaptobenzoate-S)mercury sodium salt) (Sigma Chemical Company, St. Louis, Mo.) or physiologically acceptable preservatives.\

Additional, a human or other animal may be treated for exposure to a toxin, illustratively VX, by administering an effective amount of a non-wild-type OPAA of the invention. An "effective amount" is optionally between about 0.05 to about 1000 µg/mL of a non-wild-type OPAA. A suitable dosage may be about 1.0 mL of such an effective amount. Such a composition may be administered 1-3 times per day over a 1 day to 12 week period. However, suitable dosage adjustments may be made by the attending physician or veterinarian depending upon the age, sex, weight and general health of the subject. Such a composition is optionally administered parenterally, optionally intramuscularly or subcutaneously. However, it may also be formulated to be administered by any other suitable route, including orally or topically.

As used herein, the terms "subject" or "organism" are treated synonymously and are defined as any being that includes a gene, including a virus. A subject illustratively includes: a mammal including humans, non-human primates, horses, goats, cows, sheep, pigs, dogs, cats, and rodents; arthropods; single celled organisms illustratively bacteria; viruses; and cells.

In some embodiments, a process of decontaminating a surface is provided. Such processes include contacting a surface that includes one or more toxins, illustratively VX, with a non-wild-type OPAA. Any delivery mechanism for contacting a surface with non-wild-type OPAA is operable including spraying, immersing, or other contact mechanism. The non-wild-type OPAA is optionally delivered in any form described above, illustratively as an aqueous solution. A non-wild-type OPAA is optionally maintained in contact with a surface for a contact period sufficient to catalyze degradation, optionally complete degradation, of the toxin present on the surface.

Methods involving conventional biological techniques are described herein. Such techniques are generally known in the art and are described in detail in methodology treatises such as Molecular Cloning: A Laboratory Manual, 2nd ed., vol. 1-3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, NY, 1992 (with periodic updates). Immunological methods (e.g., preparation of antigen-specific antibodies, immunoprecipitation, and immunoblotting) are described, e.g., in Current Protocols in Immunology, ed. Coligan et al., John Wiley & Sons, NY, 1991; and Methods of Immunological Analysis, ed. Masseyeff et al., Wiley & Sons, NY, 1992.

Various aspects of the present invention are illustrated by the following non-limiting examples. The examples are for illustrative purposes and are not a limitation on any practice of the present invention. It will be understood that variations and modifications can be made without departing from the spirit and scope of the invention. A person of ordinary skill in the art readily understands where any and all necessary reagents may be commercially obtained.

EXAMPLES

Example 1

Production of OPAA Mutant Sequences

A truncated version of the OPAA gene was chemically synthesized with the cloning sites RcaI and EcoRI and subsequently cloned into the respective sites in a pSE420 expression vector (Life Technologies Grand Island, N.Y.). Two initial sites were selected for mutagenesis in OPAA—Y212 and Y292. The tyrosines of these sites were mutated to an A, C, D, E, F, G, H, K, L, M, N, P, Q, S, T, V, or W. A pair of single site saturation libraries were created at these sited by incorporating degeneracies into a nucleic acids sequence at that codon.

An *E. coli* DH5α culture containing the OPAA containing the pSE420 plasmid was grown at 37° C. in 10 L of LB containing 0.1 mg/mL ampicillin and 0.1 mM $MnCl_2$. Cells were grown to mid-log phase (A600=0.5) and induced with 1 mM IPTG. After four hours of induction, the cells were harvested by centrifugation. The pellet was resuspended 0.1 mM $MnCl_2$ and 10 mM Bis-Tris Propane, pH 8 (Buffer A) and disrupted by three passages through a French pressure cell. After removing cell debris by centrifugation, the crude lysate was precipitated with $(NH_4)_2SO_4$ at 40-65% saturation. The precipitated protein was resuspended and dialyzed extensively versus buffer A. The protein solution was loaded onto a Q-Sepharose column (3×14.5 cm) and the column washed with 0.2 M NaCl in buffer A to remove unbound proteins. OPAA was eluted with a linear gradient of 0.2 to 0.6 M NaCl in buffer A. Fractions containing OPAA were precipitated with 65% $(NH_4)_2SO_4$ and dialyzed extensively against buffer A.

Example 2

Activity of Non-wild-type OPAA Constructs Against Various Agents

The hydrolysis of diisopropyl fluorophosphate (DFP) by OPAA was measured by following the release of fluoride using a fluoride specific electrode for 8 minutes. The assay was performed at 25° C. with continuous stirring in 2.5 mL of 3 mM DFP substrate, 0.1 mM $MnCl_4$, 50 mM ammonium carbonate (pH 8.0) and 0.45 μg (0.03 pM) of enzyme. A reaction without enzyme was performed to measure the background hydrolysis of DFP.

Additional assays are performed to determine the ability of each non-wild-type OPAA against a V-agent substrate. All assays were conducted in a volume of 500 μL in 1 mL cuvettes. The assay mixture consisted of 50 mM bis-tris-propane buffer, pH 8.0, 100 μM cobalt chloride and 0.3 mM 5,5'-dithiobis-(2-nitrobenzoic acid), enzyme (0.57 to 3.81 mg/ml) and V-agent substrate. The release of the thiol product of V-agent hydrolysis was followed by spectrophotometer at 412 nm absorbance.

Results for the hydrolysis of respective V-agents VM, VR, CVX (diethylamino-ethyl-O-butyl methylphosphonothioate), and VX by the respective non-wild-type OPAA constructs are presented in FIG. 1. Replacing the tyrosine at position 212 with A, D, F, G, H, K, M, P, Q, S, T, or V increases the catalytic activity toward VX. The greatest improvements are seen by replacing Y212 with F, P, Q and T. These data demonstrate that altering position 212 with particular amino acids can produce an enzyme that significantly turns over VX.

The same assays are repeated using the constructed OPAA with amino acid substitutions at Y292. The results are depicted in FIG. 2. Mutations at this position fail to show extensive improvement of activity. Collectively these results illustrate that specific mutations a position 212 will improve activity OPAA toward VX.

The Y212 mutants were subjected to heat denaturation by heating to 95° C. for 10 minutes. The treated Y212 mutants showed a loss of catalytic activity further demonstrating that the increase in catalytic activity observed using the mutant enzymes was due to enzyme activity and not to other components in a buffer system.

It is appreciated that all reagents are obtainable by sources known in the art unless otherwise specified.

Various modifications of the present invention, in addition to those shown and described herein, will be apparent to those skilled in the art of the above description. Such modifications are also intended to fall within the scope of the appended claims.

Patents and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

We claim:

1. A non-wild-type organophosphorus acid anhydrolase protein, comprising: a non-wild-type amino acid at sequence position 212, wherein said protein comprises the amino acid sequence of SEQ ID NO: 2.

2. The protein of claim 1, wherein said protein is isolated.

3. The protein of claim 1, wherein said protein has an increased catalytic activity for the degradation f (ethyl {2-[bis (propan-2-yl)amino]ethyl}sulfanyl) (methyl)phosphinate relative to the wild-type enzyme.

4. The protein of claim 3, wherein said catalytic activity is 2-fold or greater than the wild-type enzyme.

* * * * *

SEQUENCE LISTING

```
<160> NUMBER OF SEQ ID NOS: 3

<210> SEQ ID NO 1
<211> LENGTH: 517
<212> TYPE: PRT
```

<213> ORGANISM: Artificial Sequence
<220> FEATURE:
<223> OTHER INFORMATION: Organophosphorus acid anhydrolase from Altermonas sp. JD6.5

<400> SEQUENCE: 1

```
Met Asn Lys Leu Ala Val Leu Tyr Ala Glu His Ile Ala Thr Leu Gln
1               5                   10                  15

Lys Arg Thr Arg Glu Ile Ile Glu Arg Glu Asn Leu Asp Gly Val Val
            20                  25                  30

Phe His Ser Gly Gln Ala Lys Arg Gln Phe Leu Asp Asp Met Tyr Tyr
        35                  40                  45

Pro Phe Lys Val Asn Pro Gln Phe Lys Ala Trp Leu Pro Val Ile Asp
    50                  55                  60

Asn Pro His Cys Trp Ile Val Ala Asn Gly Thr Asp Lys Pro Lys Leu
65                  70                  75                  80

Ile Phe Tyr Arg Pro Val Asp Phe Trp His Lys Val Pro Asp Glu Pro
                85                  90                  95

Asn Glu Tyr Trp Ala Asp Tyr Phe Asp Ile Glu Leu Leu Val Lys Pro
            100                 105                 110

Asp Gln Val Glu Lys Leu Leu Pro Tyr Asp Lys Ala Arg Phe Ala Tyr
        115                 120                 125

Ile Gly Glu Tyr Leu Glu Val Ala Gln Ala Leu Gly Phe Glu Leu Met
    130                 135                 140

Asn Pro Glu Pro Val Met Asn Phe Tyr His Tyr His Arg Ala Tyr Lys
145                 150                 155                 160

Thr Gln Tyr Glu Leu Ala Cys Met Arg Glu Ala Asn Lys Ile Ala Val
                165                 170                 175

Gln Gly His Lys Ala Ala Arg Asp Ala Phe Phe Gln Gly Lys Ser Glu
            180                 185                 190

Phe Glu Ile Gln Gln Ala Tyr Leu Leu Ala Thr Gln His Ser Glu Asn
        195                 200                 205

Asp Asn Ala Tyr Gly Asn Ile Val Ala Leu Asn Glu Asn Cys Ala Ile
    210                 215                 220

Leu His Tyr Thr His Phe Asp Arg Val Ala Pro Ala Thr His Arg Ser
225                 230                 235                 240

Phe Leu Ile Asp Ala Gly Ala Asn Phe Asn Gly Tyr Ala Ala Asp Ile
                245                 250                 255

Thr Arg Thr Tyr Asp Phe Thr Gly Glu Gly Glu Phe Ala Glu Leu Val
            260                 265                 270

Ala Thr Met Lys Gln His Gln Ile Ala Leu Cys Asn Gln Leu Ala Pro
        275                 280                 285

Gly Lys Leu Tyr Gly Glu Leu His Leu Asp Cys His Gln Arg Val Ala
    290                 295                 300

Gln Thr Leu Ser Asp Phe Asn Ile Val Asp Leu Ser Ala Asp Glu Ile
305                 310                 315                 320

Val Ala Lys Gly Ile Thr Ser Thr Phe Phe Pro His Gly Leu Gly His
                325                 330                 335

His Ile Gly Leu Gln Val His Asp Val Gly Gly Phe Met Ala Asp Glu
            340                 345                 350

Gln Gly Ala His Gln Glu Pro Pro Glu Gly His Pro Phe Leu Arg Cys
        355                 360                 365

Thr Arg Lys Ile Glu Ala Asn Gln Val Phe Thr Ile Glu Pro Gly Leu
    370                 375                 380
```

```
Tyr Phe Ile Asp Ser Leu Leu Gly Asp Leu Ala Ala Thr Asp Asn Asn
385                 390                 395                 400

Gln His Ile Asn Trp Asp Lys Val Ala Glu Leu Lys Pro Phe Gly Gly
                405                 410                 415

Ile Arg Ile Glu Asp Asn Ile Ile Val His Glu Asp Ser Leu Glu Asn
                420                 425                 430

Met Thr Arg Glu Leu Arg Ala Arg Leu Thr Thr His Ser Leu Arg Gly
            435                 440                 445

Leu Ser Ala Pro Gln Phe Ser Ile Asn Asp Pro Ala Val Met Ser Glu
    450                 455                 460

Tyr Ser Tyr Pro Ser Glu Pro Leu Ser Tyr Glu Glu Glu Ile Lys Lys
465                 470                 475                 480

Ser Thr Phe Ile Val His Val Arg Thr Arg Arg Ile Leu Val Arg Arg
                485                 490                 495

Arg Thr Leu Ser Pro Ile Leu Ile Ala Val Thr Pro Met Pro Ala Ile
                500                 505                 510

Thr Ala Gly Leu Met
            515

<210> SEQ ID NO 2
<211> LENGTH: 440
<212> TYPE: PRT
<213> ORGANISM: Artificial Sequence
<220> FEATURE:
<223> OTHER INFORMATION: Synthetic mutant OPAA Y212F

<400> SEQUENCE: 2

Met Asn Lys Leu Ala Val Leu Tyr Ala Glu His Ile Ala Thr Leu Gln
1               5                   10                  15

Lys Arg Thr Arg Glu Ile Ile Glu Arg Glu Asn Leu Asp Gly Val Val
                20                  25                  30

Phe His Ser Gly Gln Ala Lys Arg Gln Phe Leu Asp Asp Met Tyr Tyr
            35                  40                  45

Pro Phe Lys Val Asn Pro Gln Phe Lys Ala Trp Leu Pro Val Ile Asp
    50                  55                  60

Asn Pro His Cys Trp Ile Val Ala Asn Gly Thr Asp Lys Pro Lys Leu
65                  70                  75                  80

Ile Phe Tyr Arg Pro Val Asp Phe Trp His Lys Val Pro Asp Glu Pro
                85                  90                  95

Asn Glu Tyr Trp Ala Asp Tyr Phe Asp Ile Glu Leu Leu Val Lys Pro
            100                 105                 110

Asp Gln Val Glu Lys Leu Leu Pro Tyr Asp Lys Ala Arg Phe Ala Tyr
        115                 120                 125

Ile Gly Glu Tyr Leu Glu Val Ala Gln Ala Leu Gly Phe Glu Leu Met
    130                 135                 140

Asn Pro Glu Pro Val Met Asn Phe Tyr His Tyr His Arg Ala Tyr Lys
145                 150                 155                 160

Thr Gln Tyr Glu Leu Ala Cys Met Arg Glu Ala Asn Lys Ile Ala Val
                165                 170                 175

Gln Gly His Lys Ala Ala Arg Asp Ala Phe Phe Gln Gly Lys Ser Glu
            180                 185                 190

Phe Glu Ile Gln Gln Ala Tyr Leu Leu Ala Thr Gln His Ser Glu Asn
        195                 200                 205

Asp Thr Pro Phe Gly Asn Ile Val Ala Leu Asn Glu Asn Cys Ala Ile
    210                 215                 220
```

```
Leu His Tyr Thr His Phe Asp Arg Val Ala Pro Ala Thr His Arg Ser
225                 230                 235                 240

Phe Leu Ile Asp Ala Gly Ala Asn Phe Asn Gly Tyr Ala Ala Asp Ile
            245                 250                 255

Thr Arg Thr Tyr Asp Phe Thr Gly Glu Gly Glu Phe Ala Glu Leu Val
        260                 265                 270

Ala Thr Met Lys Gln His Gln Ile Ala Leu Cys Asn Gln Leu Ala Pro
        275                 280                 285

Gly Lys Leu Tyr Gly Glu Leu His Leu Asp Cys His Gln Arg Val Ala
        290                 295                 300

Gln Thr Leu Ser Asp Phe Asn Ile Val Asn Leu Ser Ala Asp Glu Ile
305                 310                 315                 320

Val Ala Lys Gly Ile Thr Ser Thr Phe Phe Pro His Gly Leu Gly His
            325                 330                 335

His Ile Gly Leu Gln Val His Asp Val Gly Gly Phe Met Ala Asp Glu
            340                 345                 350

Gln Gly Ala His Gln Glu Pro Pro Glu Gly His Pro Phe Leu Arg Cys
        355                 360                 365

Thr Arg Lys Ile Glu Ala Asn Gln Val Phe Thr Ile Glu Pro Gly Leu
370                 375                 380

Tyr Phe Ile Asp Ser Leu Leu Gly Asp Leu Ala Ala Thr Asp Asn Asn
385                 390                 395                 400

Gln His Ile Asn Trp Asp Lys Val Ala Glu Leu Lys Pro Phe Gly Gly
            405                 410                 415

Ile Arg Ile Glu Asp Asn Ile Ile Val His Glu Asp Ser Leu Glu Asn
            420                 425                 430

Met Thr Arg Glu Leu Glu Leu Asp
        435                 440

<210> SEQ ID NO 3
<211> LENGTH: 1320
<212> TYPE: DNA
<213> ORGANISM: Artificial Sequence
<220> FEATURE:
<223> OTHER INFORMATION: Synthetic encoding mutant OPAA

<400> SEQUENCE: 3
atgaacaaac tggcggtgct gtatgcggaa catattgcga ccctgcagaa acgcacccgc    60
gaaattattg aacgcgaaaa cctggatggc gtggtgtttc atagcggcca ggcgaaacgc   120
cagtttctgg atgatatgta ttatccgttt aaagtgaacc gcagtttaa agcgtggctg   180 ccggtgattg ataacccgca ttgctggatt gtggcgaacg gcaccgataa accgaaactg   240 atttttatc gcccggtgga ttttggcat aaagtgccgg atgaaccgaa cgaatattgg   300
gcggattatt ttgatattga actgctggtg aaaccggatc aggtggaaaa actgctgccg   360
tatgataaag cgcgctttgc gtatattggc gaatatctgg aagtggcgca ggcgctgggc   420
tttgaactga tgaacccgga accggtgatg aactttatc attatcatcg cgcgtataaa   480
acccagtatg aactggcgtg catgcgcgaa gcgaacaaaa ttgcggtgca gggccataaa   540
gcggcgcgcg atgcgttttt tcagggcaaa agcgaattg aaattcagca ggcgtatctg   600
ctggcgaccc agcatagcga aaacgatacc ccgtttggca cattgtggc gctgaacgaa   660 aactgcgcga ttctgcatta tacccatttt gatcgcgtgg cgccggcgac ccatcgcagc   720
tttctgattg atgcgggcgc gaactttaac ggctatgcgg cggatattac cgcaccctat   780
gattttaccg gcgaaggcga atttgcggaa ctggtggcga ccatgaaaca gcatcagatt   840
```

```
gcgctgtgca accagctggc gccgggcaaa ctgtatggcg aactgcatct ggattgccat      900
cagcgcgtgg cgcagaccct gagcgatttt aacattgtga acctgagcgc ggatgaaatt      960
gtggcgaaag gcattaccag cacctttttt ccgcatggcc tgggccatca tattggcctg     1020
caggtgcatg atgtgggcgg ctttatggcg gatgaacagg gcgcgcatca ggaaccgccg     1080
gaaggccatc cgtttctgcg ctgcacccgc aaaattgaag cgaaccaggt gtttaccatt     1140
gaaccgggcc tgtattttat tgatagcctg ctgggcgatc tggcggcgac cgataacaac     1200
cagcatatta actgggataa agtggcggaa ctgaaaccgt ttggcggcat tcgcattgaa     1260
gataacatta ttgtgcatga agatagcctg gaaaacatga cccgcgaact ggaactggat     1320
```